United States Patent [19]

Harada et al.

[11] 4,135,100

[45] Jan. 16, 1979

[54] METHOD AND APPARATUS FOR DETECTING CONCENTRATION OF LIQUID

[75] Inventors: Yoshiaki Harada, Hachioji; Kazuo Okamura, Kanagawa; Masahiro Kondo, Hachioji all of Japan

[73] Assignee: Konishiroku Photo Industry Co., Ltd., Tokyo, Japan

[21] Appl. No.: 821,204

[22] Filed: Aug. 2, 1977

[30] Foreign Application Priority Data

Aug. 6, 1976 [JP] Japan .................................. 51/93172

[51] Int. Cl.² .......................................... G01N 21/26
[52] U.S. Cl. .................................... 250/573; 356/440
[58] Field of Search ........... 250/358, 573, 574, 237 R; 356/201, 204, 207, 208

[56] References Cited

U.S. PATENT DOCUMENTS

| 3,255,441 | 6/1966 | Goodwin et al. | 250/573 |
| 3,306,157 | 2/1967 | Hach | 356/208 |
| 3,879,129 | 4/1975 | Inoue | 356/208 |

Primary Examiner—David C. Nelms
Attorney, Agent, or Firm—Bierman & Bierman

[57] ABSTRACT

A method and apparatus is disclosed for determining the concentration of a liquid. A net or lattice screen member is dipped into a liquid and pulled out therefrom. Light rays are then transmitted through a liquid curtain formed on the net or lattice screened member in order to optically determine the concentration of said liquid.

4 Claims, 7 Drawing Figures

METHOD AND APPARATUS FOR DETECTING CONCENTRATION OF LIQUID

The present invention relates to a method and an apparatus for detecting the concentration of a liquid.

A typical known method for detecting and measuring the concentration of a liquid comprises passing the liquid through a transparent path, irradiating said path with light rays and measuring photoelectrically the quantity of transmitted rays to determine the concentration. According to this method, the transparent path is readily contaminated with an adhering solid contained in the liquid, such as a toner. Therefore, this conventional method is defective in that as frequency of empolyment increases, even if the practical concentration is gradually lowered, it is impossible to obtain correct measurement results. As means for overcoming this defect, there has been proposed a method in which a wall or enclosure is not used for the liquid path but a liquid curtain or so-called water curtain is formed and the concentration is detected in a space hardly contacted with the water curtain. According to this method, the liquid stream is regulated by a controlling member to form a liquid curtain, but contamination of this controlling member with the liquid cannot be completely prevented and a photo-electric converter element or light source is contaminated with splashes of the liquid. Therefore, it is impossible to perform the measurement precisely, and it is necessary to provide an air curtain or a plate member to prevent the liquid from splashing.

Each of the foregoing known measurement methods depends on optical means for determination, and a common problem involved in the methods using the optical means is that since the output of the light source or power source is changed with the lapse of time and is unstable, the intensity of the projected light is changed after a long time or at short time intervals and it is difficult to always obtain precise concentration measurement results. As a countermeasure for eliminating this disadvantage, there has already been proposed a method in which a photoelectric element for the standard light is disposed in the vicinity of the light source in addition to the photoelectric element used directly for the measurement, rays from the light source are applied directly to the photoelectric element for the standard light, rays transmitted through a liquid, for example, a liquid developer, are received by the photoelectric element for the measurement and output signals of both the photo-electric elements are compared with each other so as to perform the measurement precisely. In this method, however, it is difficult to provide two photo-electric elements having quite the same characteristics and even if two such photo-electric elements can be provided, it will be further difficult to arrange them so that changes of the characteristics with the lapse of time are quite the same in the two elements. Moreover, since the two photo-electric elements are disposed at different positions, the same light intensities cannot be obtained from these elements and it is therefore necessary to make a correction of the intensity between the two elements.

It is therefore a primary object of the present invention to provide a method quite different from the foregoing conventional methods for measuring concentration of liquid according to which method defects involved in the conventional methods are eliminated or remarkably improved.

In accordance with the fundamental aspect of the present invention, there is provided a method for detecting concentration of liquid which comprises dipping a net or lattice screen member in the liquid of which the concentration is to be measured, pulling out the screen member from the liquid, forming a liquid curtain on a net or lattice of the screen member, and transmitting light rays through said liquid curtain to thereby detect optically the concentration of the liquid. More specifically, when a net or lattice screen member is dipped in the liquid and pulled out from the liquid, a liquid curtain is formed on the net or lattice of the screen member by the surface tension, and this screen member is then introduced into an optical detection zone and light rays are transmitted through the so formed liquid curtain to thereby measure optically the concentration of the liquid. According to this method, contact with a liquid developer is reduced as much as possible so as to prevent contamination with a toner in the liquid developer, and a large quantity of the liquid developer can be retained in the detection zone. Therefore, the method of the present invention is very convenient and economically advantageous as the method for determining the concentration of the liquid developer or the like. In the method of the present invention, a liquid-free space portion is formed on a part of the screen member, and the quantity of light rays passing through the liquid curtain and the quantity of light rays passing through this space portion are photo-electrically detected and compared with each other to determine the concentration of the liquid. According to the method of the present invention, since the screen member is dipped in the liquid at every measurement, contamination of a light source or photo-electric element with the splashing liquid is hardly caused, and therefore, an air curtain or a liquid splashing preventing plate need not be provided at all. Further, since measurement rays from the light source are not transmitted through the screen member and the screen member per se is not constructed so as to participate directly in the measurement, even if it is used frequently and becomes contaminated, measurement is not influenced at all by toner particles adhering in a direction parallel to the transmitted light rays. Of course, stains adhering to the screen member in a direction perpendicular to the transmitted light rays may make the measurement incorrect more or less, but they can be removed completely and easily by the cleaning operation. Moreover, since only one photo-electric element is sufficient for the measurement, in addition to a fundamental merit of a cheap running cost, there is attained a merit that characteristics of the photo-electric element in use, the change thereof with the lapse of time and the mounting position of the photo-electric element need not be taken into consideration. Still further, any compensating circuit need not be disposed so as to cope with the temperature drifts in the photo-electric element.

According to the present invention, since a liquid curtain is formed by the surface tension of the liquid, thickness of the liquid curtain can be remarkably reduced. Accordingly, liquid having such a high concentration as cannot be measured by the conventional methods can easily be treated with in the present invention and the concentration can be determined precisely.

As the screen member, there can be employed a woven wire screen, a screen prepared by electro-forming, a screen prepared by photo-etching, and the like. There are many kinds of woven wire screens differing in materials and mesh number, and they are advantageous in that desirable screens can optionally be chosen and they are not expensive. However, woven wire screens have a defect that mesh arrangement is not regular and noises are caused by an irregular mesh arrangement. With screens prepared by electro-forming or photo-etching, a regular mesh arrangement can be attained and a mesh pattern having a high opening ratio enabling retention of a large quantity of liquid can be formed. A screen prepared by photo-etching is advantageous over a screen prepared by electro-forming in the point that the screen thickness can be increased and a larger quantity of liquid, therefore, can be retained.

In the present invention, fineness (mesh number) of the net or lattice of the screen member has a close relation to either the liquid retention time or the fog density (sensitivity) at the measurement. The finer the net or lattice, more stably the liquid is retained on the screen member but the less the amount retained of the liquid or the change of the concentration. In view of the foregoing, a screen having a net or lattice of 50 to 200 mesh is practically preferred. When it is desired to increase the sensitivity of measurement of the concentration of the liquid, it is necessary to coarsen the mesh pattern of the net or lattice. Namely, it is necessary to decrease the mesh number in the net or lattice. The lower limit of the mesh number is appropriately determined depending on whether or not the liquid can be retained on the screen member at the measurement.

Embodiments of the present invention will now be described by reference to the accompanying drawings in which.

Incidentally, the embodiments given hereinafter relate to the detection of the concentration of a liquid developer, but it must be noted that the present invention is not limited to this feature but it can be applied broadly for determination of concentrations of various liquids as well.

Figure 1:
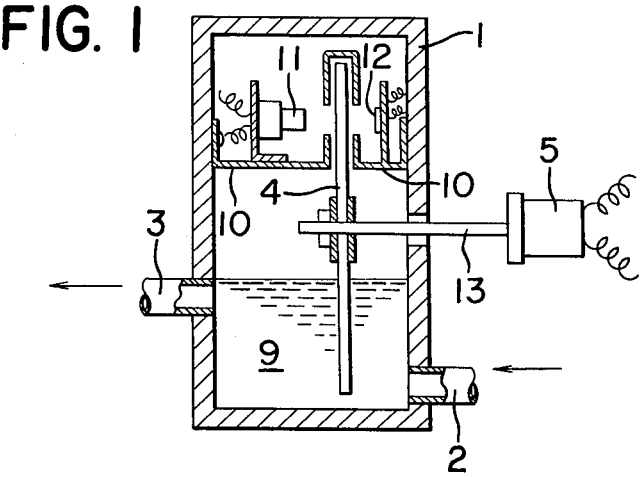
FIG. 1 is a pictorial sectional view showing the liquid concentration detecting apparatus of the present invention.
Figure 2:
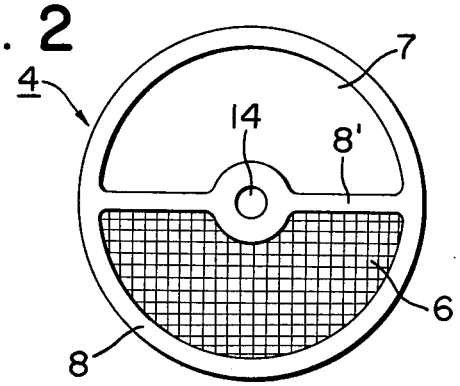
FIGS. 2 to 4 are views showing examples of the screen members that can be used in the present invention.

Referring now to FIG. 1 which illustrates the section of the apparatus for detecting the concentration of a liquid developer according to the present invention, a detection zone 1 includes an introduction port 2 for branching a liquid developer from a supply pipe at the time of the measurement and introducing the branched liquid developer into a detecting cell and a discharge port 3 for discharging the liquid developer from the detecting cell after the measurement. In the interior of the detection zone 1, a screen member 4 is disposed so that it can be rotated by an electric motor 5 mounted outside the detection zone 1. FIG. 2 ilustrates one example of the screen members available for the invention which 4 is composed of a circular frame 8 and a partition frame 8' including a liquid curtain-forming portion 6 formed of a net or lattice and a space portion 7.

Figure 3:
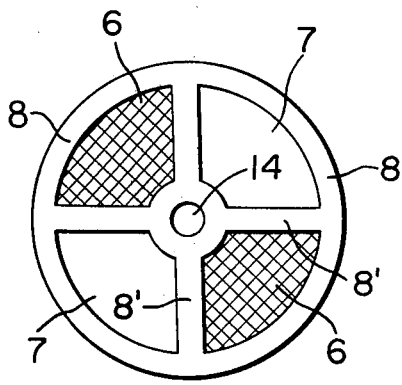
Figure 4:
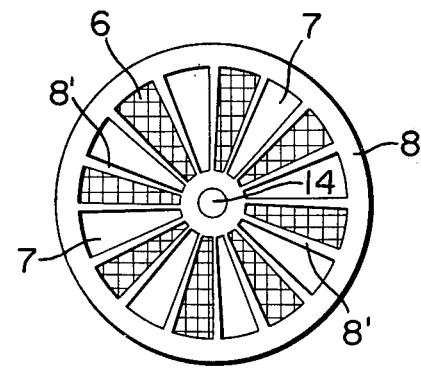

Other examples of the screen member usable for the present invention are illustrated in FIGS. 3 and 4. The screen member shown in FIG. 3 comprises a circular frame 8, a pair of liquid curtain-forming portions 6 and a pair of space portions 7, these portions 6 and 7 having the same area and being arranged alternately with a partition frame 8' interposed therebetween. The screen member shown in FIG. 4 comprises a circular frame 8, a plurality of liquid curtain-forming portions 6 and a plurality of space portions 7, these portions 6 and 7 having the same area and being arranged alternately. Adjacent two portions 6 and 7 are separated by a partition frame 8'.

Figure 5:
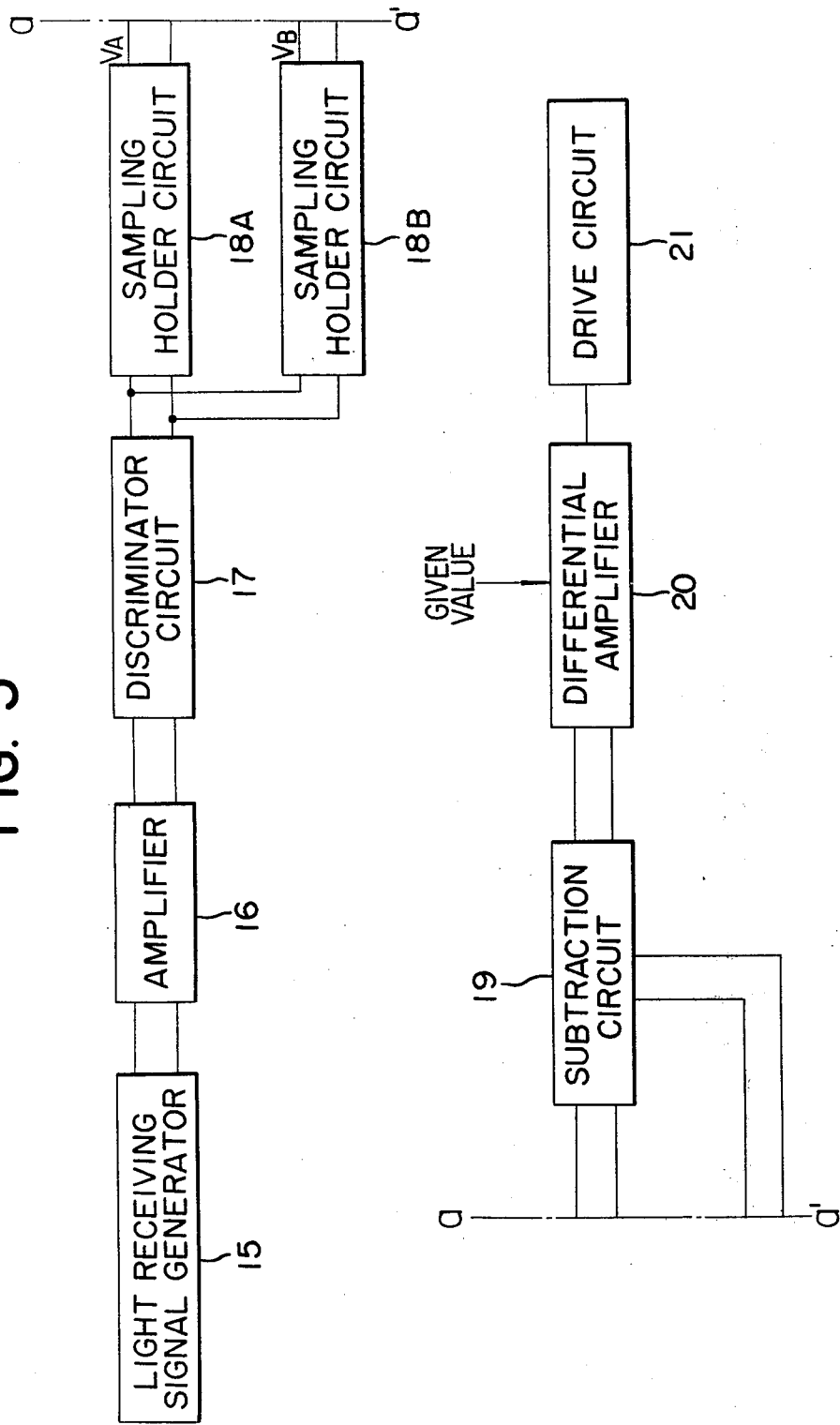
FIG. 5 is a block diagram of a measurement circuit for providing outputs of the liquid concentration detecting apparatus of the present invention.

Referring again to FIG. 1 of the drawings, the detecting cell 1, is filled with a liquid developer 9 to such an extent of depth that the lower half of the circular screen member 4 is dipped in the liquid developer 9. A light source 11 and a light receiving element 12 such as a photo-cell are disposed on a supporting plate 10 fixed to the side wall in the upper half space inside the detecting cell 1 so that they confront each other with the screen member 4 interposed therebetween. The light source 11 is connected to an appropriate power source (not shown), and the light receiving element 12 is connected to a detection circuit as shown in FIG. 5. A hole 14 is formed at the center of the screen member 4 so that a driving shaft 13 driven by the electric motor 5 is put into this hole 14.

Detection of the concentration of a liquid developer is conducted in the following manner with the liquid concentration apparatus having the above-mentioned structure.

Figure 6:
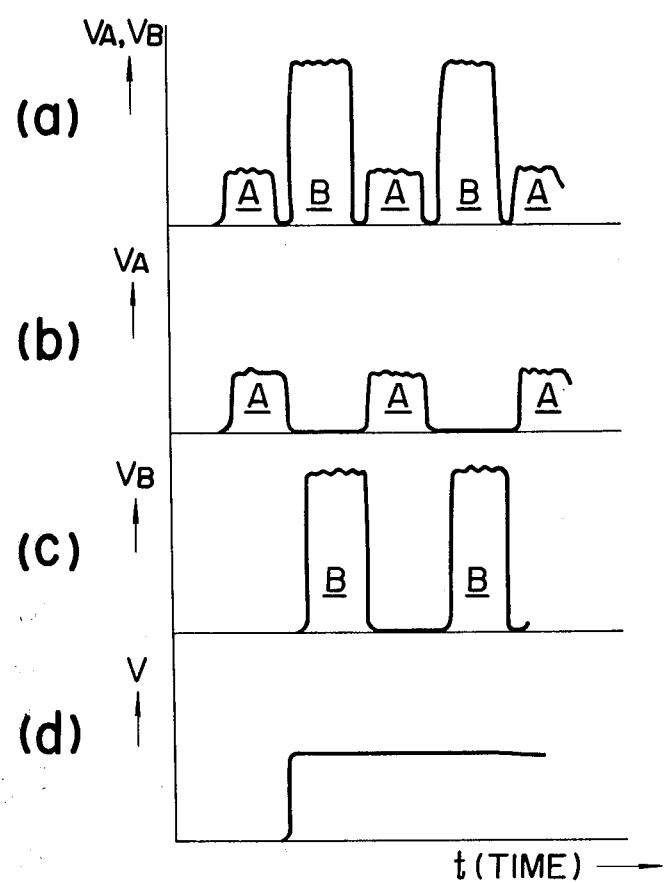
FIG. 6 is a diagram illustrating waveforms of output signals of respective constituent elements in the measurement circuit shown in FIG. 5.

When the screen member 4 (one such as shown in FIG. 2) is rotated by actuating the electric motor 5 continuously or intermittently, the liquid curtain-forming portion 6 and space portion 7 of the screen member 4 pass alternately through the optical axis defined by the light source 11 and the light receiving element 12. When the liquid curtain-forming portion 6 traverses this optical axis, a liquid curtain of the liquid developer is formed on the net or lattice by the surface tension and the light is projected onto the light receiving element 12 in a quantity determined according to the concentration of the liquid developer. When the space portion 7 of the screen member 4 traverses the optical axis, all the light of the light source 11 is directly projected onto the light receiving element 12. When a solar battery is used as the light receiving element 12, the output thereof has a signal waveform as shown in FIG. 6 (a), in which two waves A and B are those formed when the liquid curtain-forming portion 6 and the space portion 7 traverse the optical axis, alternately. The solar battery is used so that the characteristics thereof are included in the region of the linearly corrected waveform.

Based on the so obtained signals, reduction of the concentration in the liquid developer is detected by a detection circuit as shown in the block diagram of FIG. 5. In FIG. 5, two sections are joined at the line a—a' to complete the detection circuit. Two kinds of signals obtained by a light receiving signal generator 15 are amplified by an amplifier 16 and discriminated into two sampling holder circuits 18A and 18B by a discriminator circuit 17. The so discriminated two signals A and B are shown in FIGS. 6 (b) and 6 (c). Each sampling holder circuit has an analogue switch and holds only the signal portion. The difference $V_D$ between the two outputs $V_A$ and $V_B$ of the sampling holder circuits 18A and 18B is obtained from a subtraction circuit 19:

$$V_D = K(V_B - V_A) \quad (1)$$

wherein K stands for a proportional constant, $V_A$ denotes the voltage of the output associated with the liquid curtain-forming portion 6 and $V_B$ designates the voltage of the output associated with the space portion 7.

Since the outputs are obtained by a pair of optical means as pointed out hereinbefore, any difference caused by components in phase and changes with the lapse of time can be simultaneously eliminated. The output $V_D$ of the subtraction circuit 19 is compared with a predetermined value $V_P$ in a differential amplifier 20 and the resulting signal is fed to a final drive circuit 21. Since the output $V_A$ associated with the liquid curtain-forming portion 6 increases with reduction of the concentration in the liquid developer, the output $V_D$ of the subtraction circuit 19 is reduced, and when the following relation is established between the output $V_D$ of the subtraction circuit 19 and the above-mentioned predetermined value $V_P$:

$$V_D < V_P \quad (2)$$

the drive circuit is operated to supply a concentrated liquid developer, whereby reduction of the concentration of the liquid developer below a predetermined level is prevented.

The above-mentioned measurement circuit will be described in detail by reference to a specific example shown in FIG. 7.

Figure 7:
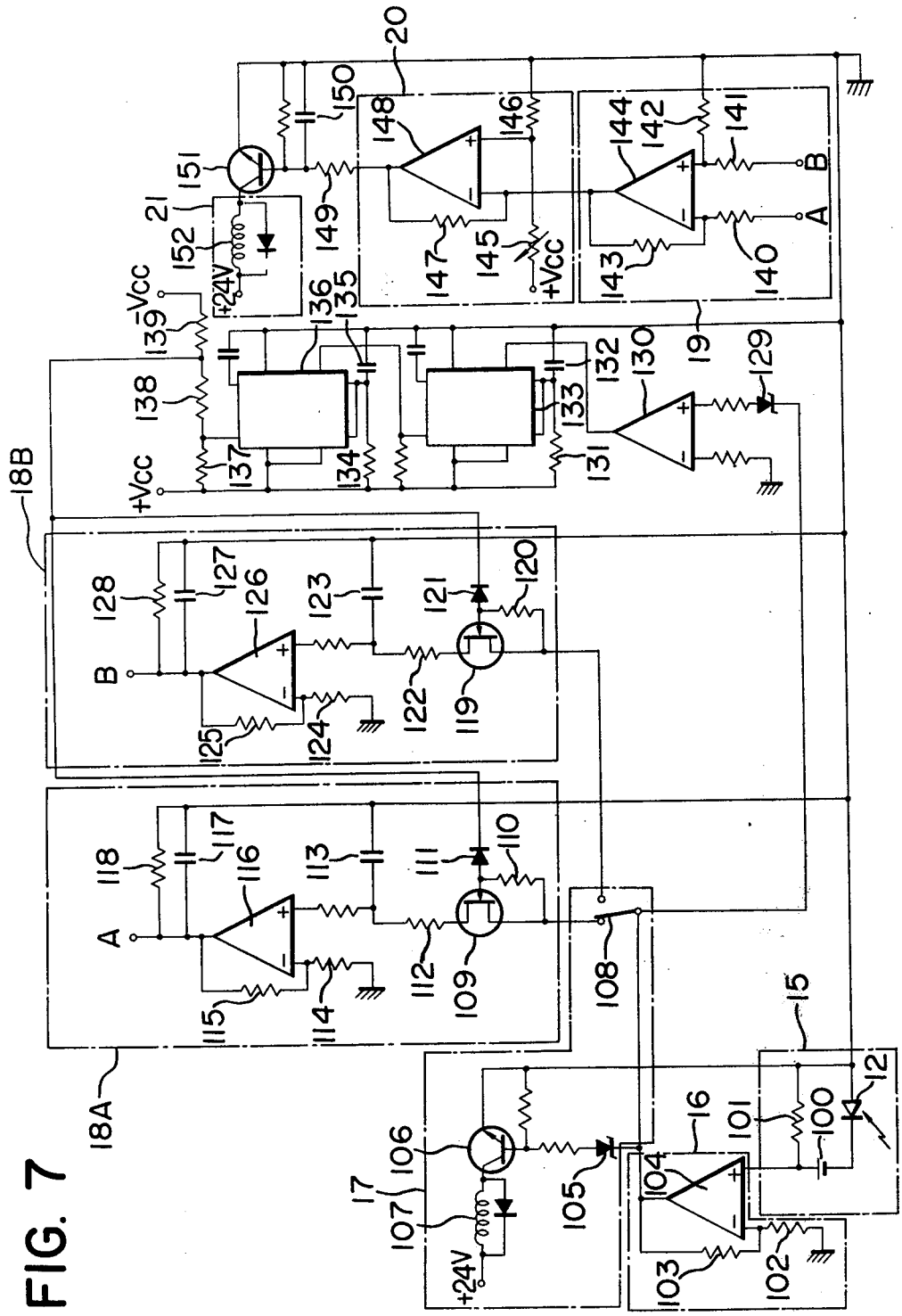
FIG. 7 is a view showing one specific example of the measurement circuit shown in FIG. 5.

Referring now to FIG. 7, the above-mentioned solar battery is represented by reference numeral 12, and a light-receiving signal-generating zone 15 comprises this solar battery 12, a power source 100 and a resistor 101. The output of an amplifier 104 compares the voltages $V_A$ and $V_B$ of the above-mentioned signals A and B with a zener voltage $V_Z$ of a zener diode 105 and sets degree of amplification so that the following relation is established:

$$V_A < V_Z \text{ and } V_B < V_Z \quad (3)$$

This amplification degree is decided by resistors 102 and 103. The discriminator circuit 17 shown in FIG. 5 comprises the zener diode 105, a transistor 106, an actuating coil 107 and a change-over switch 108. Only when the signal B is emitted, the transistor 106 turns on to energize the actuating coil 107 (relay). The change-over switch 108 consisting of a contact of the relay 107 discriminates the signals A and B into two sampling holder circuits 18A and 18B, each comprising a field effect transistors (FET) 109 or 119, a capacitor 113 or 123, an amplifier 116 or 126 and a capacitor 117 or 127 connected across a resistor 118 or 128. The two sampling holder circuits 18A and 18B are quite the same, and each consists of an analogue switch including the field effect transistor 109 or 119, a resistor 110 or 120 and a diode 111 or 121, an integrating circuit including a resistor 112 or 122 and the capacitor 113 or 123 and a hold circuit including resistors 114 and 115 or 124 and 125, the amplifier 116 or 126, the capacitors 117 or 127 and the resistor 118 or 128. "ON" signals are added to gates of the field effect transistors 109 and 119 of the respective analog switches from gate input-generating zones (129 to 139), and when these "ON" signals are added, the analog switches are switched on to hold the signals A and B as samples. In the above circuit, the gate input-generating zone comprises a transistor 130 and two monostable multi-vibrators 133 and 136. The level of the zener voltage of the zener diode 129 is shifted so that it becomes lower than the voltages $V_A$ and $V_B$ of the signals A and B, and when the above signals A and B are sufficiently raised, the amplifier 130 generates a rectangular wave for triggering the mono-stable multi-vibrator 133. The time constant of the mono-stable multi-vibrator 133 is decided by a resistor 131 and a capacitor 132 so that it corresponds to the time during which the partition frame 8' of the screen member 4 passes through the gap between the light source 11 and the light receiving element 12. The time constant of the mono-stable multi-vibrator 136 is determined by a resistor 134 and a capacitor 135 so that it corresponds to the length of the time of the signals A and B. By this arrangement, an output having a waveform as shown in FIG. 6 (d) is generated from the gate input-generating zone and the field effect transistors 109 and 119 are turned on only during the passage times of the signals A and B, respectively. The voltages $V_A$ and $V_B$ held in the foregoing manner are put into the subsequent differential amplifier 20 (including members represented by reference numerals 145 to 148) as an output proportional to the difference represented by the above formula (1) by the subtraction circuit 19. The output is compared with a predetermined voltage corresponding to an allowable lowest concentration of the liquid developer by this differential amplifier 20, and when it exceeds the predetermined value $V_P$ for determining whether the drive circuit (including members 149 to 152) is switched on or off and the relation represented by the formula (2) is established, a transistor 151 is actuated to operate a relay 152. By actuating a solenoid or the like for supplying a concentrated liquid developer by the operation of this relay 152, the concentration is immediately restored to a predetermined high level when the concentration of the liquid developer is reduced. A resistor 149 and a capacitor 150 constitute an integrating circuit for preventing an erroneous operation when the light power is actuated.

The output signal of the measurement circuit is added to a differential amplifier (not shown) or the like and is then fed to a liquid developer concentration display device or a liquid developer concentration adjusting device.

As will be apparent from the foregoing illustration, in the present invention, since the output of the measurement circuit is obtained by transmitting light rays from one light source onto one light receiving element and comparing the output signal corresponding to the liquid curtain-forming portion of the screen member with the output signal corresponding to the space portion of the screen member, the concentration can be detected precisely irrespective of changes of the intensity of the light from the light source or changes of characteristics of the light receiving element, and any further correction need not be conducted at all in the later stage.

The present invention can be applied to the measurement of the concentration of liquid having such a viscosity as being capable of forming a light curtain on a net or lattice, and the screen member that is used in the present invention may be of either the type which is continuously rotated as in the foregoing embodiments or the type which is intermittently dipped or immersed in the liquid. In the present invention, the area ratio of the liquid curtain-forming portion to the space portion, the time for dipping the screen member in the liquid and the dipping frequency may be determined appropriately depending on the kind and concentration of the liquid.

What we claim is:

1. A method for detecting concentration of liquid which comprises dipping a net or lattice screen member in the liquid of which concentration is to be measured, pulling out the screen member from the liquid, and transmitting light rays through a liquid curtain formed on a net or lattice of the screen member, to thereby detect optically the concentration of the liquid.

2. An apparatus for detecting concentration of liquid which comprises a detecting cell for containing therein the liquid of which concentration is to be measured, a net or lattice screen member having a liquid curtain-forming portion, driving means for driving said screen member so that the liquid curtain-forming portion of said screen member is dipped in the liquid in the detecting cell and then pulled out from the liquid, and a light source and a photoelectric converter element which are disposed to confront each other with the screen member interposed therebetween.

3. An apparatus as set forth in claim 2 wherein said screen member is provided with a space portion in an alternate relation with said liquid curtain-forming portion and further comprising a discriminator circuit for discriminating an output of said photoelectric convertor to provide a first electric signal associated with said liquid curtain-forming portion of said screen member and a second electric signal associated with said space portion of said screen member; two sampling holder circuits for holding said first and second electrical signals; a subtraction circuit for providing difference between said first and second signals and a concentrated developer replenishing device adapted to be actuated when the output of said subtraction circuit decreases below a predetermined level.

4. An apparatus as set forth in claim 2 wherein a space portion not forming a liquid curtain is formed on said screen member and a measurement circuit including a comparator for comparing an electric signal corresponding to the quantity of light rays transmitted through the liquid curtain-forming portion with an electric signal corresponding to the quantity of light rays transmitted through the space portion is further provided.

* * * * *